US010741292B2

(12) United States Patent
Lai et al.

(10) Patent No.: US 10,741,292 B2
(45) Date of Patent: Aug. 11, 2020

(54) REMOTE MEDICAL ANALYSIS

(71) Applicant: Vet24seven Inc., Mountain View, CA (US)

(72) Inventors: Calbert Lai, Mountain View, CA (US); Kevin Hultquist, San Jose, CA (US); Annette Puskarich, Palo Alto, CA (US); Russell Jong, Palo Alto, CA (US); Edward Blach, Monument, CO (US); Treve Williams, Elizabeth Bay (AU)

(73) Assignee: VET24SEVEN INC., Mountain View, CA (US)

( * ) Notice: Subject to any disclaimer, the term of this patent is extended or adjusted under 35 U.S.C. 154(b) by 569 days.

(21) Appl. No.: 14/740,044

(22) Filed: Jun. 15, 2015

(65) Prior Publication Data

US 2015/0363564 A1 Dec. 17, 2015

Related U.S. Application Data

(60) Provisional application No. 62/012,150, filed on Jun. 13, 2014.

(51) Int. Cl.
*G16H 80/00* (2018.01)
*A61D 99/00* (2006.01)
(Continued)

(52) U.S. Cl.
CPC ............. *G16H 80/00* (2018.01); *A61D 99/00* (2013.01); *G16H 10/60* (2018.01); *G16H 40/67* (2018.01)

(58) Field of Classification Search
CPC .. G06Q 50/22; G06Q 10/1095; G06Q 10/109; G06Q 30/018; G06Q 99/00;
(Continued)

(56) References Cited

U.S. PATENT DOCUMENTS 6,006,191 A * 12/1999 DiRienzo .............. G06F 19/321
705/2
6,208,974 B1 * 3/2001 Campbell ............. G06F 19/328
705/3

(Continued)

FOREIGN PATENT DOCUMENTS

WO 2010/148444 12/2010

OTHER PUBLICATIONS

Mars, M. and Auer, R.E.J , "Telemedicine in veterinary practice," Journal of the South African Veterinary Association, vol. 77, No. 2, pp. 75-78 (Jun. 2006). (Year: 2006).*

*Primary Examiner* — Rachel L. Porter
(74) *Attorney, Agent, or Firm* — David R. Stevens; Stevens Law Group

(57) ABSTRACT

The present invention extends to methods, systems, and computer program products for remote medical analysis. Advances in mobile devices offer a way to connect animals and veterinarians in ways other than physical proximity. Using a phone's camera to take photos or and/or video and send those to a veterinarian allows greater degree of detail to be communicated in triaging or diagnosing or follow-up for an animal. Additionally, the camera could be used to conduct a video chat between an animal owner and a veterinarian allowing real-time viewing and conversation between the two parties.

17 Claims, 18 Drawing Sheets

(51) Int. Cl.
*G16H 10/60* (2018.01)
*G16H 40/67* (2018.01)

(58) Field of Classification Search
CPC .. G06Q 10/06; G06Q 10/06314; G06Q 10/10; G06Q 10/1093; G06Q 10/1097; G06Q 20/10; G06Q 30/00; G06Q 30/0235; G06Q 30/0601
USPC .......................................................... 705/2, 3
See application file for complete search history.

(56) References Cited

U.S. PATENT DOCUMENTS

| | | | |
|---|---|---|---|
| 2001/0051765 A1* | 12/2001 | Walker | A61B 5/1112 600/300 |
| 2011/0054978 A1* | 3/2011 | Mohil | G06Q 10/06 705/7.18 |
| 2013/0173439 A1* | 7/2013 | Christiansen | G06Q 10/103 705/34 |
| 2013/0013333 A1 | 10/2013 | Gopinathan et al. | |
| 2013/0317838 A1 | 11/2013 | Schoenberg | |
| 2014/0019162 A1* | 1/2014 | Skowronski | G06Q 50/24 705/3 |
| 2014/0052463 A1* | 2/2014 | Cashman | G06Q 20/18 705/2 |
| 2014/0058755 A1 | 2/2014 | Macoviak et al. | |

* cited by examiner

- 441
- EMAIL 401
- USERNAME 402
- PASSWORD 403
- REGISTER FOR AN ACCOUNT 404

FIG.4B

MY ANIMALS
MY VETS
LOGOUT
REPORT BUGS & FEEDBACK
ABOUT VET24SEVEN

NAME
ADDRESS
PHONE
PICTURE
EMAIL
PASSWORD
PAYMENT

DROP DOWN LIST 407

DROPDOWN LIST 406

GET HELP FROM A VETERINARIAN 442

BACK    NEXT

FIG.4C

ABOUT YOUR ANIMAL

ANIMAL'S NAME 408

AGE — LESS THAN ONE YEAR 409
SPECIES — SELECT 411
BREED — SELECT 412
GENDER — SELECT 413

UPLOAD YOUR ANIMAL'S PICTURE
UPLOAD 414
443

ADD ANIMAL 416

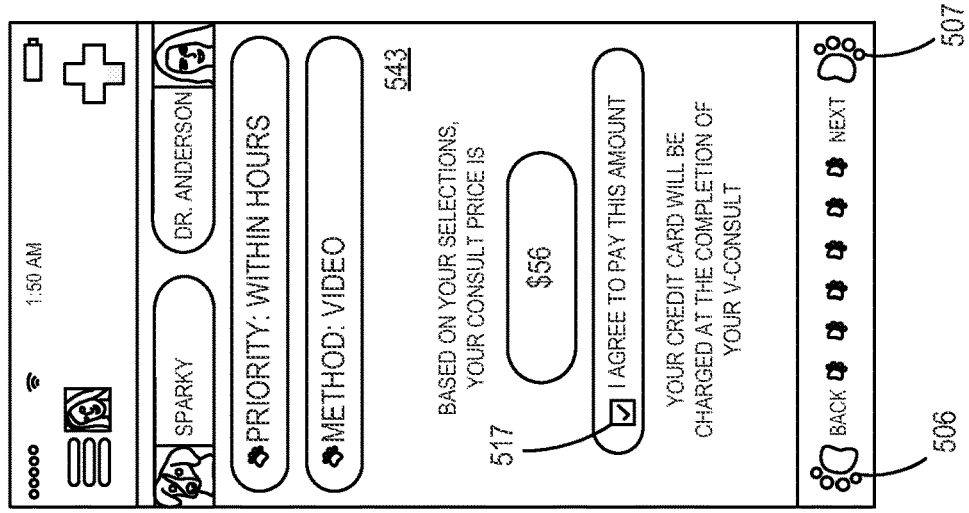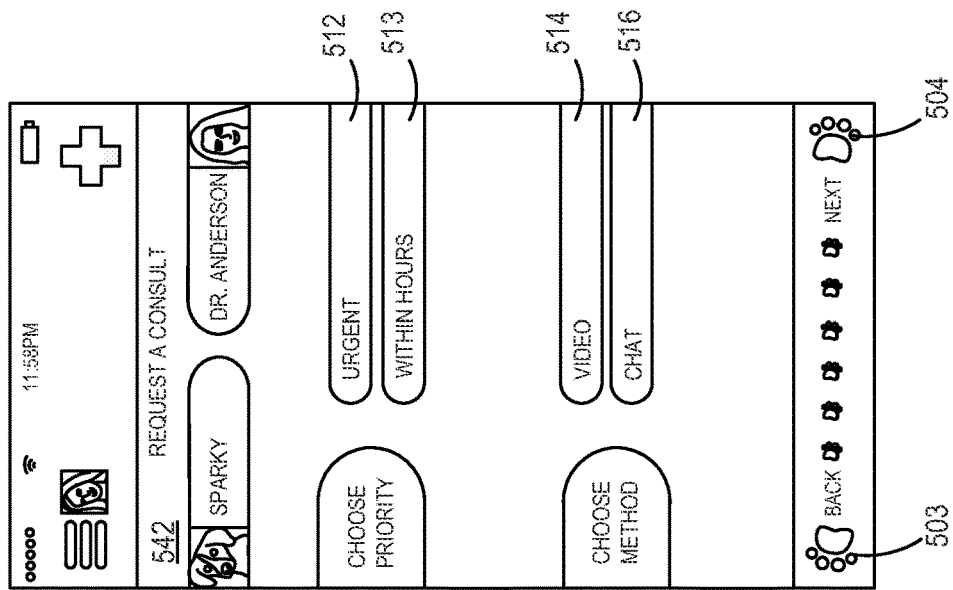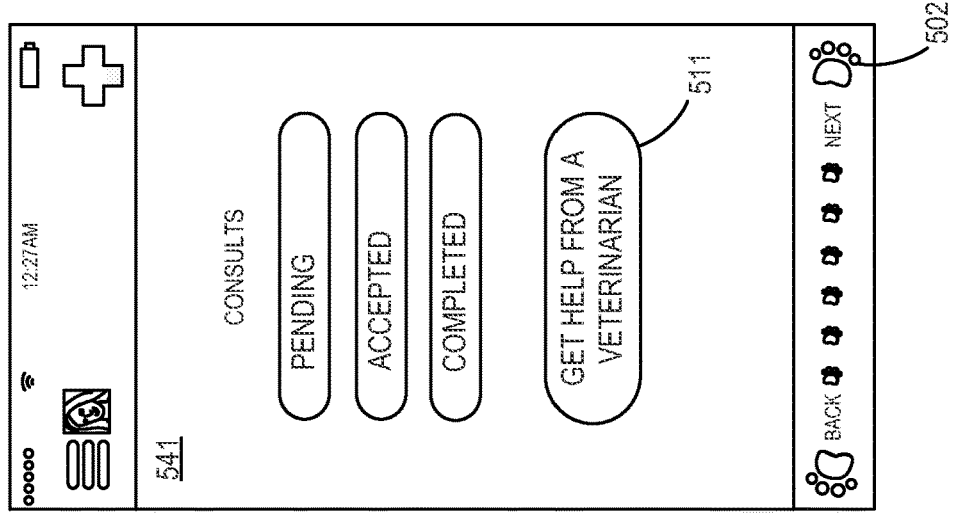

VETERINARY CONSULT REQUEST FOR SPARKY (DOG) REFERENCE # VK7E3WEVOT

CUSTOMER CARE <CUSTOMERCARE@TEST.COM>
TO ME ▽

HELLO DR. ANDERSON,

YOU HAVE RECEIVED A VETERINARY CONSULT (V-CONSULT) REQUEST FOR SPARKY

PLEASE FIND BELOW THE DETAILS OF YOUR V-CONSULT REQUEST:
V-CONSULT REFERENCE #VK7E3WEVOT
PATIENT: SPARKY
SPECIES: DOG
CLIENT: MARY SMITH
NATURE OF V-CONSULT: TESTING
PRIORITY: WITHIN HOURS
METHOD: VIDEO
CLIENT IS EXPECTING RESPONSE BY: 2015/05/19 04:00AM

IF YOU ARE UNABLE TO RESPOND TO THIS CONSULT REQUEST, PLEASE USE THE REFERENCE # ABOVE TO LOCATE THIS CONSULT IN YOUR DASHBOARD AND ALLOW IT TO BE ASSIGNED TO ANOTHER VETERINARIAN.

IF YOU HAVE QUESTION, PLEASE CONTACT TEST CUSTOMER CARE AT
CUSTOMERCARE@TEST.COM

THANK YOU,
THE TEAM

CONTACT WITH US:
EMAIL: CUSTOMERCARE@TEST.COM
PHONE: 888-888-8888
WEB: WWW.TEST.COM
TWITTER: @TEST
FACEBOOK: FACEBOOK.COM/TEST

FIG.5F

DR. SAMANATHA SARAH SMITH
PET AND PAWS
123 MAIN ST. STE. 345
ST. HELENA, CA 94574, USA

BUSINESS HOURS

| | | | |
|---|---|---|---|
| MONDAY | OPEN | 09:00AM | 06:00PM |
| TUESDAY | OPEN | 09:00AM | 06:00PM |
| WEDNESDAY | OPEN | 09:00AM | 06:00PM |
| THURSDAY | CLOSED | 08:00AM | N/A |
| FRIDAY | OPEN | 09:00AM | 06:00PM |
| SATURDAY | CLOSED | N/A | N/A |
| SUNDAY | CLOSED | N/A | N/A |

AVAILABLE ( EDIT )

DR. SAMANATHA SARAH SMITH
PET AND PAWS
123 MAIN ST. STE. 345
ST. HELENA, CA 94574, USA

CONSULTING RATES PER CONSULT

| | WITHIN HOURS | URGENT | AFTER BUSINESS HOURS |
|---|---|---|---|
| VIDEO | $20 | $45 | $55 |
| CHAT | $35 | $45 | $55 |

( EDIT )

FIG. 7B

REMOTE MEDICAL ANALYSIS

CROSS-REFERENCE TO RELATED APPLICATIONS

This application claims the benefit of U.S. Provisional Patent Application No. 62/012,150, entitled "Remote Medical Analysis", filed Jun. 13, 2014, which is incorporated herein in its entirety.

BACKGROUND

1. Field of the Invention

This invention relates generally to the field of remote medical analysis, and, more particularly, to veterinary consultations.

2. Related Art

When an animal is need of medical attention, the animal's owner typically takes the animal to a veterinarian for evaluation and treatment. For larger animals, a veterinarian may instead go to the location of the animal and evaluate and treat the animal there. However, it can often be difficult to get a qualified veterinarian and an animal in the same physical location for any number of reasons. For example, the distance needed to transport the animal may be too great, no qualified veterinarian may be available for the type of animal requiring assistance, an animal's medical condition or mood may prevent transportation, the animal may be too large to transport, etc.

BRIEF DESCRIPTION OF THE DRAWINGS

The specific features, aspects and advantages of the present invention will become better understood with regard to the following description and accompanying drawings where:

FIG. 3B illustrates an example of how to enter subjective findings related to a veterinary consult.

FIG. 3C illustrates an example of how to enter objective findings related to a veterinary consult.

FIG. 3D illustrates an example of how to enter a veterinarian assessment related to a veterinary consult.

FIGS. 4A-4G illustrate user interface screens used to register a client with a network-based veterinary service provider.

FIGS. 5A-5F illustrate user interface screens associated with requesting a veterinary consult.

FIG. 7A illustrates availability for a veterinarian.

FIG. 7B illustrates a pricing matrix for a veterinarian.

DETAILED DESCRIPTION

Figure 1:
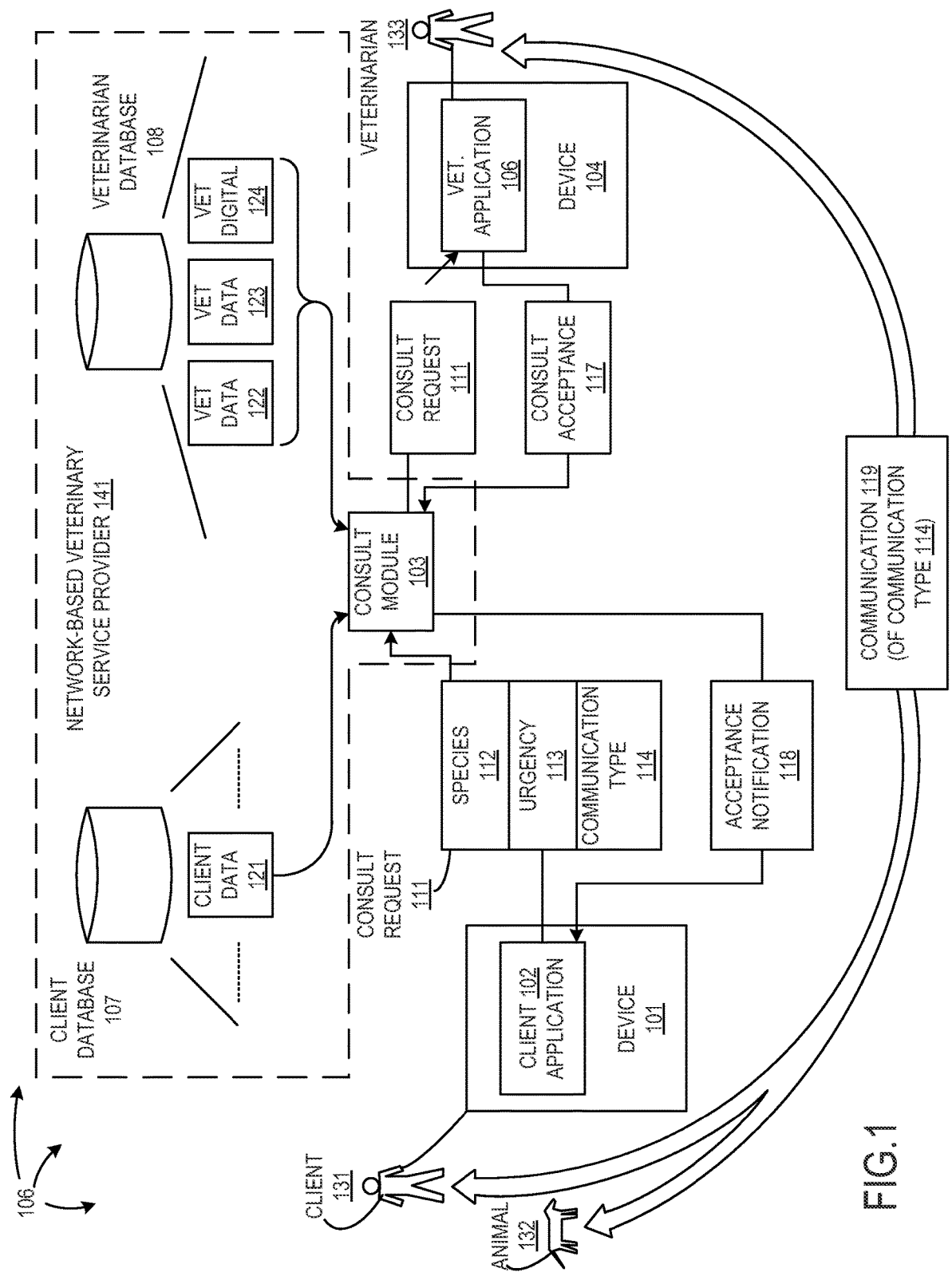
FIG. 1 illustrates an example computer architecture that facilitates remote medical analysis.

The present invention extends to methods, systems, and computer program products for remote medical analysis.

Embodiments of the invention include remote medical analysis of animals by veterinarians. Clients can use a client application to register with a network-based veterinary service provider. Client registration can include submitting client data, such as, for example, contact information (e.g., name, mailing address, email, etc.), username, password, billing information (e.g., credit card information), associations with any veterinary clinics, etc. and agreeing to terms of service. Clients can also setup animal profiles for one or more animals, including animal profile information (e.g., name, age, specifies, breed, genera, photo, etc.). Client data, including animal profiles, can be stored in a client database of the network-based veterinary service provider.

Veterinarians can use a veterinarian application to register with the network-based veterinary service provider. Veterinarian registration can include submitting veterinarian data, such as, for example, name, address, phone number, single or multiple veterinarian practice, species treated, credentials, any specialties, licenses, direct deposit information (for receiving payments), clinic information when applicable, a personal statement, etc. Veterinarian data can be stored in a veterinarian database of the network-based veterinary service provider.

Subsequent to client registration, a client can use the client application to submit a request for a veterinary consult to the network-based veterinary service provider. Generally, the request for a veterinary consult is a request for veterinary medical analysis with respect to a condition of an animal. The veterinary consult request can include an animal species, an urgency, and a preferred network communication type (e.g., text message, real-time video, etc.). The network-based veterinary service provider can receive the veterinary consult request from the client application.

The network-based veterinary service provider can access client data for the client from the client database. The network-based veterinary service provider can also access veterinarian data for one or more veterinarians from the veterinarian database. The network-based veterinary service provider can match the veterinary consult request to one or more relevant veterinarians based on one or more of: the animal species, the urgency, the preferred network communication type, the client information, and the veterinarian information. Each of the one or more relevant veterinarians can be notified of the availability of the veterinary consult at their corresponding veterinary application. A veterinarian can accept the veterinary consult through the veterinary application. The veterinarian application can send a notification to the network-based veterinary service provider indicating that the veterinarian has accepted the veterinary consult.

The network-based veterinary service provider can receive the notification from the veterinarian application of the accepting veterinarian. The network-based veterinary service provider can then send a corresponding notification to the client application indicating that the veterinarian has accepted the veterinary consult. The client and veterinarian can exchange further communication of the preferred network communication type between the client application and veterinarian application to analyze the condition of the animal. The further communication can include electronic messaging, real-time audio and/or video communication, etc.

When the veterinary consult is complete, the payment information for the client is used to bill the client a specified fee. A portion of the specified fee is retained by the network-based veterinary service provider in exchange for use of the platform. The remainder of the specified fee is remitted to the veterinarian, for example, using the direct deposit information.

After a veterinary consult is complete, the client and the veterinarian are provided an option to rate one another.

In one aspect, the mobile devices with audio/video (A/V) communication capabilities, such as, for example, smart phones are used to connect animals and veterinarians in ways other than physical proximity. Using a mobile device's camera to take photos and/or video and send those to a veterinarian permits greater degree of detail to be communicated in triaging or diagnosing or follow-up for an animal. Additionally, a camera can be used to conduct a video chat between an animal owner and a veterinarian allowing real-time viewing and conversation between the two parties.

In the following description of the present invention, reference is made to the accompanying drawings, which form a part hereof, and in which is shown by way of illustration specific embodiments in which the invention is may be practiced. It is understood that other embodiments may be utilized and structural changes may be made without departing from the scope of the present invention.

Embodiments of the present invention may comprise or utilize a special purpose or general-purpose computer including computer hardware, such as, for example, one or more processors and system memory, as discussed in greater detail below. Embodiments within the scope of the present invention also include physical and other computer-readable media for carrying or storing computer-executable instructions and/or data structures. Such computer-readable media can be any available media that can be accessed by a general purpose or special purpose computer system. Computer-readable media that store computer-executable instructions are computer storage media (devices). Computer-readable media that carry computer-executable instructions are transmission media. Thus, by way of example, and not limitation, embodiments of the invention can comprise at least two distinctly different kinds of computer-readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to computer storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. RAM can also include solid state drives (SSDs or PCIx based real time memory tiered Storage, such as FusionIO). Thus, it should be understood that computer storage media (devices) can be included in computer system components that also (or even primarily) utilize transmission media.

Computer-executable instructions comprise, for example, instructions and data which, when executed at a processor, cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, various storage devices, and the like. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Devices can have touch screens as well as other I/O components.

The described aspects can also be implemented in cloud computing environments. In this description and the following claims, "cloud computing" is defined as a model for enabling on-demand network access to a shared pool of configurable computing resources. For example, cloud computing can be employed in the marketplace to offer ubiquitous and convenient on-demand access to the shared pool of configurable computing resources. The shared pool of configurable computing resources can be rapidly provisioned via virtualization and released with low management effort or service provider interaction, and then scaled accordingly.

A cloud computing model can be composed of various characteristics such as, for example, on-demand self-service, broad network access, resource pooling, rapid elasticity, measured service, and so forth. A cloud computing model can also expose various service models, such as, for example, Software as a Service ("SaaS"), Platform as a Service ("PaaS"), and Infrastructure as a Service ("IaaS"). A cloud computing model can also be deployed using different deployment models such as private cloud, community cloud, public cloud, hybrid cloud, and so forth. In this description and in the claims, a "cloud computing environment" is an environment in which cloud computing is employed.

FIG. 1 illustrates an example computer architecture 100 that facilitates remote medical analysis. Referring to FIG. 1, computer architecture 100 includes device 101, consult module 103, device 104, client database 107, and veterinarian database 108. Device 101, consult module 103, device 104, client database 107, and veterinarian database 108 can be connected to (or be part of) a network, such as, for example, a Local Area Network ("LAN"), a Wide Area Network ("WAN"), and even the Internet. Accordingly, device 101, consult module 103, device 104, client database 107, and veterinarian database 108 as well as any other connected computer systems and their components, can create message related data and exchange message related data (e.g., Internet Protocol ("IP") datagrams and other higher layer protocols that utilize IP datagrams, such as, Transmission Control Protocol ("TCP"), Hypertext Transfer Protocol ("HTTP"), Simple Mail Transfer Protocol ("SMTP"), Simple Object Access Protocol (SOAP), etc. or using other non-datagram protocols) over the network.

Device 101 can be a mobile telephone, tablet, or computer and includes client application 102. Client application 102 provides client 131 with an interface to network-based veterinary service provider 141. Client 131 can use client application 102 to register with network-based veterinary service provider 141 and to request veterinary consults from network-based veterinary service provider 141. Client 131 can use client application 102 interact with a registration module (not shown) of network-based veterinary service provider 141 to enter client data 121 during a registration process. When a veterinary consult is complete, client 131 can also use client application 102 to rate the veterinarian that performed the veterinary consult.

Client database 107 stores client data for registered clients of network-based veterinary service provider 141. For example, client database 107 can store client data 121 for client 131. Client data can include a username, email, password, name, address, phone number, and photo of a client. Client data can also include profiles for one or more animals the client cares for. Each animal profile can include a name, age, species, breed, gender, and photo for an animal.

Device 104 can be a mobile telephone, tablet, or computer and includes veterinarian application 106. Veterinarian application 106 provides veterinarian 133 with an interface to network-based veterinary service provider 141. Veterinarian 133 can use veterinarian application 106 to register with network-based veterinary service provider 141. Veterinarian 133 can also use veterinarian application 106 to view and accept available veterinary consults from network-based veterinary service provider 141. Veterinarian 133 can use veterinarian application 106 to interact with a registration module (not shown) of network-based veterinary service provider 141 to enter veterinarian data 121 during a registration process.

Veterinarian database 108 stores veterinarian data for registered veterinarians of network-based veterinary service provider 141. For example, veterinarian database 108 can store veterinarian data 122, 123, 124, etc. Veterinarian data 123 can correspond to veterinarian 133. Veterinarian data can vary depending on type of practice, such as, for example, single or multiple veterinarian, association with a clinic, etc. Veterinarian data can include practice name, practice address, practice phone number, indication of single or multiple veterinarian practice. For each veterinarian associated with a practice, veterinarian data can include a name, email, phone number, species treated, hours of availability, academic credentials, specialties (e.g., board certified), a photo, a personal statement, licenses, tax forms, and direct deposit information for the veterinarian.

In general, consult module 103 is configured to match veterinary consults requests to veterinarians suitable to handle the veterinary consults. Consult module 103 can receive veterinary consult requests from registered clients of network-based veterinary service provider 141. A veterinary consult requests can include consult data defining the parameters of the veterinary consult, such as, for example, a species, urgency, and preferred communication mechanism. Consult module 103 can refer to client data for the registered client and to veterinarian data for registered veterinarians of network-based veterinary service provider 141. Based on the consult data, the client data (including an animal profile), and the veterinarian data for registered veterinarians, consult module 103 can identify one or more veterinarians suited to handle the veterinary consult request. One of the suitable suitable veterinarians can then accept the request and perform the veterinary consult via the preferred communication mechanism. Once a veterinary consult is accepted, communications between a veterinarian and a client can be established with the same devices used to interface with network-based veterinary service provider 141 or with different devices.

Figure 2:
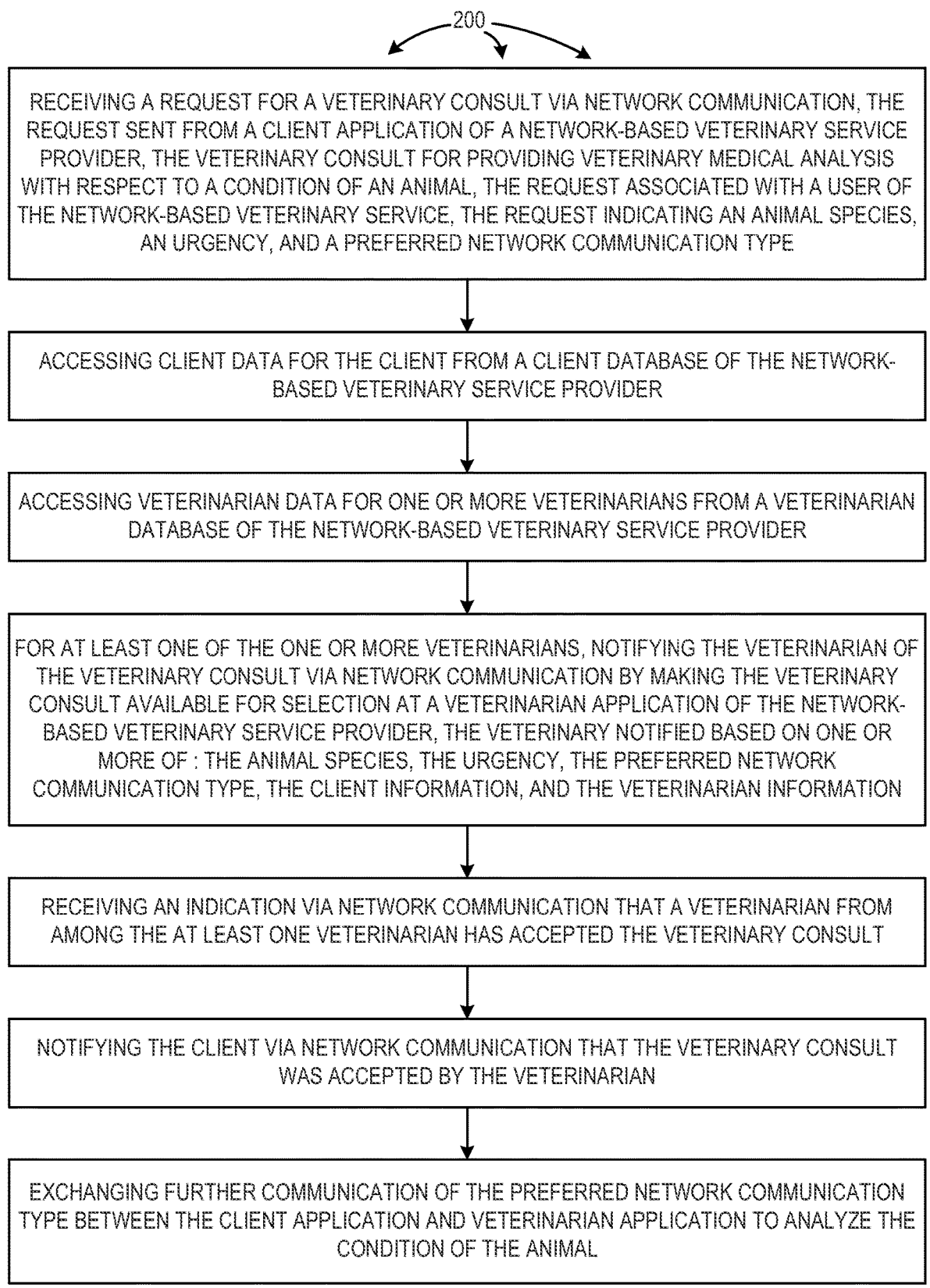
FIG. 2 illustrates a flow chart of an example method for matching items to users.

FIG. 2 illustrates a flow chart of an example method 200 for identifying a health related event. Method 200 will be described with respect to the components and data of computer architecture 100.

Client 131 can formulate consult request 111 at client application 102. Consult request 111 can be a request for a veterinary consult to provide medical analysis with respect to a condition of animal 132. Client 131 can interact with user-interface controls of client application 102 to configure consult request 111 to include species 112, urgency, 113, and communication 114. Species 112 can indicate the species (e.g., dog, cat, bird, etc.) of animal 132. Urgency 113 can indicate a time frame for when client 131 desired the veterinary consult to occur, such as, for example, in the next 15 minutes, within 4 hours, sometime today, within a day, etc. Communication type 144 indicates the type of communication preferred by client 131, such as, for example, text messages, text chat, audio, audio/video, etc., when conducting the veterinary consult.

In one aspect, client 131 also includes one or more pictures and/or one or more videos of animal 132 representative the animal 132's condition.

In another aspect, client 131 also describes animal 132's condition in one or more text fields. The one or more text fields can include a shorter text field configure to accept 2-3 words describing the animals condition. The one or more text fields can also include a longer text field configured to accept potentially unlimited text used for a more detailed description of animal 132's condition.

Client application 102 can send consult request 111 to consult module 103.

Method 200 includes receiving an request for a veterinary consult via network communication, the request sent from a client application of a network-based veterinary service provider, the veterinary consult for providing veterinary medical analysis with respect to a condition of an animal, the request initiated a client of the network-based veterinary service, the request indicating an animal species, an urgency, and a preferred network communication type (201). For example, consult module 103 can receive consult request 111 from client application 102.

Method 200 includes accessing client data for the client from a client database of the network-based veterinary service provider (202). For example, consult module 103 can access client data 121 from client database 107. Method 200 includes accessing veterinarian data for one or more veterinarians from a veterinarian database of the network-based veterinary service provider (203). For example, consult module 103 can access veterinarian data 122, 123, and 124 from veterinarian database 108.

Method 200 includes for at least one of the one or more veterinarians, notifying the veterinarian of the veterinary consult request via network communication by making the veterinary consult request available for selection at a veterinarian application of the network-based veterinary service provider, the veterinary notified based on one or more of: the animal species, the urgency, the preferred network communication type, the client data, and the veterinarian data (204). For example, consult module 103 can notify veterinarian 133 of consult request 111 by making consult request 111 available for selection at veterinarian application 106. Veterinarian 133 can be notified based on one or more of: an ability to treat animals of species 112, accepting consult request 111 within time parameters defined by urgency 113, an ability to communicate using communication type 114, veterinarian preferences contained in client data 121, availability to perform the consult within time parameters defined by urgency 113, being licensed in the jurisdiction of the animal, etc.

In one aspect, prior to notifying the one or more veterinarians, consult module 103 refers to a pricing matrix to determine a fee for the requested consult. Consult module 103 presents the fee to client application 102 for approval by client 131. If client 131 approves the fee, processing of the consult request continues. Upon approval, consult module 103 can also pre-authorize a charge to a credit card identified client data 121. If client 131 does not approve the fee, processing of the consult request can be terminated.

The price presented to a client can be a factor of a pricing matrix, business or operating hours, and method (e.g., live video or chat (messaging). For example, an urgent, live video consult during the day may be priced differently than an urgent, live video consult in the middle of the night. (see FIGS. 7A and 7B).

Veterinarian 133 can accept consult request 111 from veterinarian application 106. Veterinarian application 106 can send consult acceptance 117 to consult module 103.

Method 200 includes receiving an indication via network communication that a veterinarian from among the at least one veterinarian has accepted the veterinary consult (205). For example, consult module 103 can receive consult acceptance 117 from veterinarian application 106. Consult acceptance 117 indicates to consult module 103 that veterinarian 133 has accepted consult request 111. Method 200 includes notifying the client via network communication that the veterinary consult was accepted by the veterinarian (206). For example, consult module 103 can send acceptance notification 118 to client application 102. Acceptance notification 118 notifies client 131 that consult request 111 was accepted by veterinarian 133.

In one aspect, veterinarian 133 includes a proposed time to conduct the veterinary consult in consult acceptance 117. The proposed time can be included in acceptance notification 118. Client 131 can agree to the proposed time or propose a different time. Proposed times can be exchanged until client 131 and veterinarian 133 agree to a time.

Method 200 includes exchanging further communication of the preferred network communication type between the client application and veterinarian application to analyze the condition of the animal (207). Subsequently, for example, at around a proposed time, client 131 and veterinarian 133 can exchange further communication of communication type 114 to analyze the condition of animal 132.

During the veterinary consult, additional photos and videos can be transferred form client 131 to veterinarian 133. During veterinary consult, veterinarian application 106 can present a Subjective, Objection, Assessment, Plan form for the veterinarian 133 to edit and complete. The Subjective, Objection, Assessment, Plan form can include check boxes and note fields for selecting conditions and entering notes.

Veterinarian application 106 can email prescriptions for animal 132 to designated recipients including the client, a pharmacy, or another person. Veterinarian application 106 can also email a summary of the veterinary consult to client 132 and record the veterinary consult in a file for animal 132.

In one aspect, veterinary consults are conducted via live video or chat (messaging) within the client and veterinarian application (e.g., 102 and 106). Veterinary consults are initiated by the veterinarian. When using chat to conduct a veterinary consults, the client and veterinarian are notified when the other party sends a message. To conduct a veterinary consult via video, the veterinarian launches video chat and an invitation to join the video is sent to the client via text message and in-app message. If the client responds to the video invitation, the veterinarian connects with their client. If the client does not accept the video invitation, the client receives a notification, and the veterinarian can attempt to contact the client again. The video can have an indicator of signal strength and allow sharing of and drawing on photos. On the veterinarian application, the video can share the device screen with the SOAP form so that the veterinarian can complete the SOAP form and video consult with client in parallel.

More than two individuals can participate in a live video or chat session. The veterinarian and/or client can invite additional participants. For example, a veterinarian can invite another veterinary, for example, a specialist, into a live video or chat session. A client can invite another person interested in the care of the animal, for example, a family member, into a live video or chat session.

Both client application 102 and veterinarian application 106 can include dashboards for presenting information about veterinarian consult requests. A dashboard at client application 102 can display the status (e.g., pending, accepted, completed, canceled, etc.) of veterinarian consult requests sent from client application 102. A dashboard at veterinarian application 106 can display the status (e.g., available, accepted, completed, canceled, etc.) of veterinarian consult requests available to veterinarian 133.

Figure 3A:
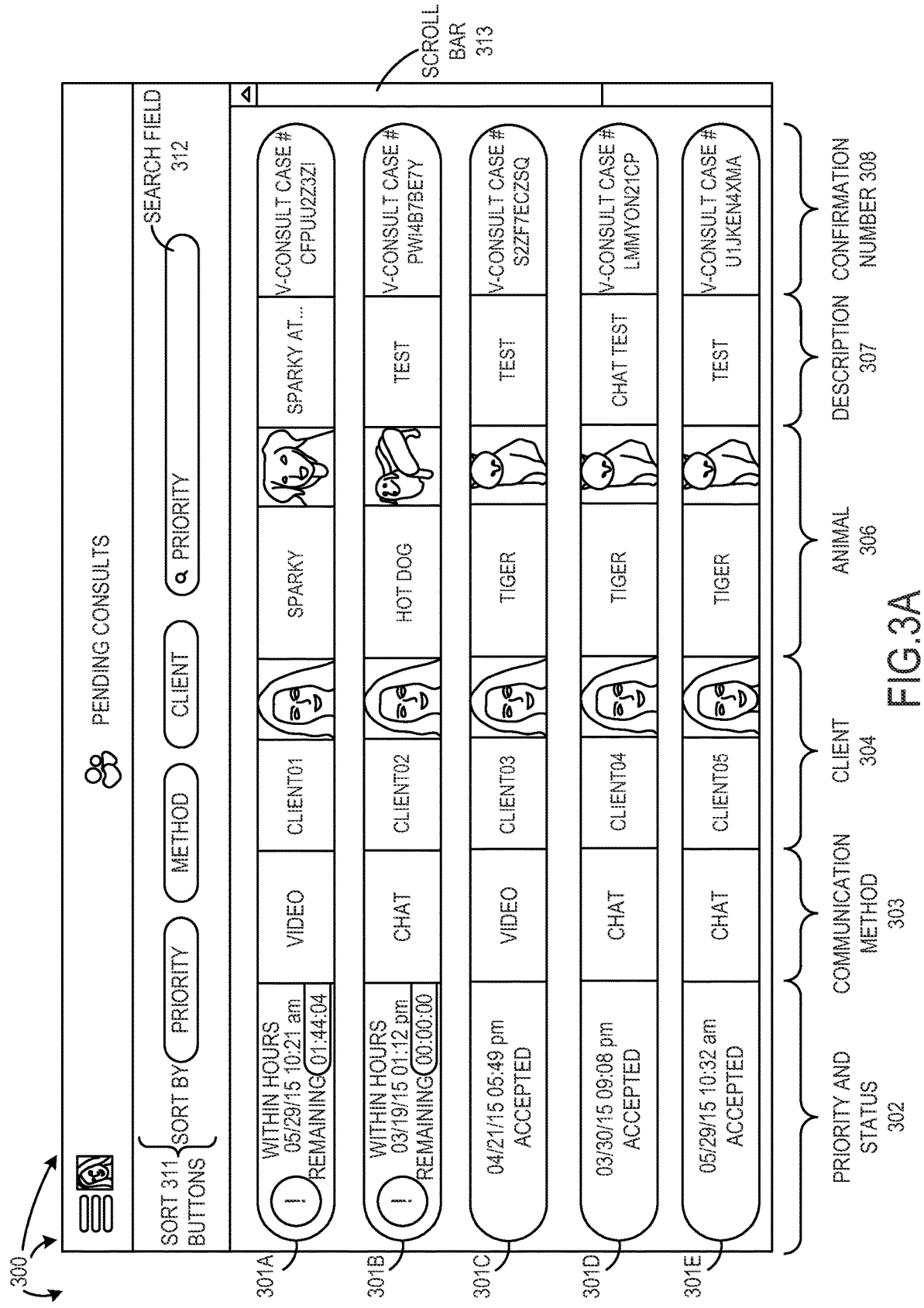
FIG. 3A illustrates an example of a veterinarian dashboard.

FIG. 3A illustrates an example of a veterinarian dashboard 300. Veterinarian application can provide a dashboard similar veterinarian dashboard 300 at device 104. As depicted, dashboard 300 is displaying veterinary consults 301A-301E. Each of veterinary consults 301A-301E indicates a priority (urgency) and status 302, a communication method 303, a client 304, an animal 306, a description 307 of the animal's condition, and a confirmation number 308. The confirmation number 308 can be used by a client, a veterinary, or a network-based veterinary service provider to reference the corresponding veterinary consult.

Dashboard 300 includes sort buttons 311, search field 312, and scroll bar 312. Sort buttons can be used to soft displayed consult request by priority, method or client. Search field 312 can be used to search for particular text with consult requests. Scroll bar 313 can be used to scroll up or down to additional consult requests.

Figure 3B:
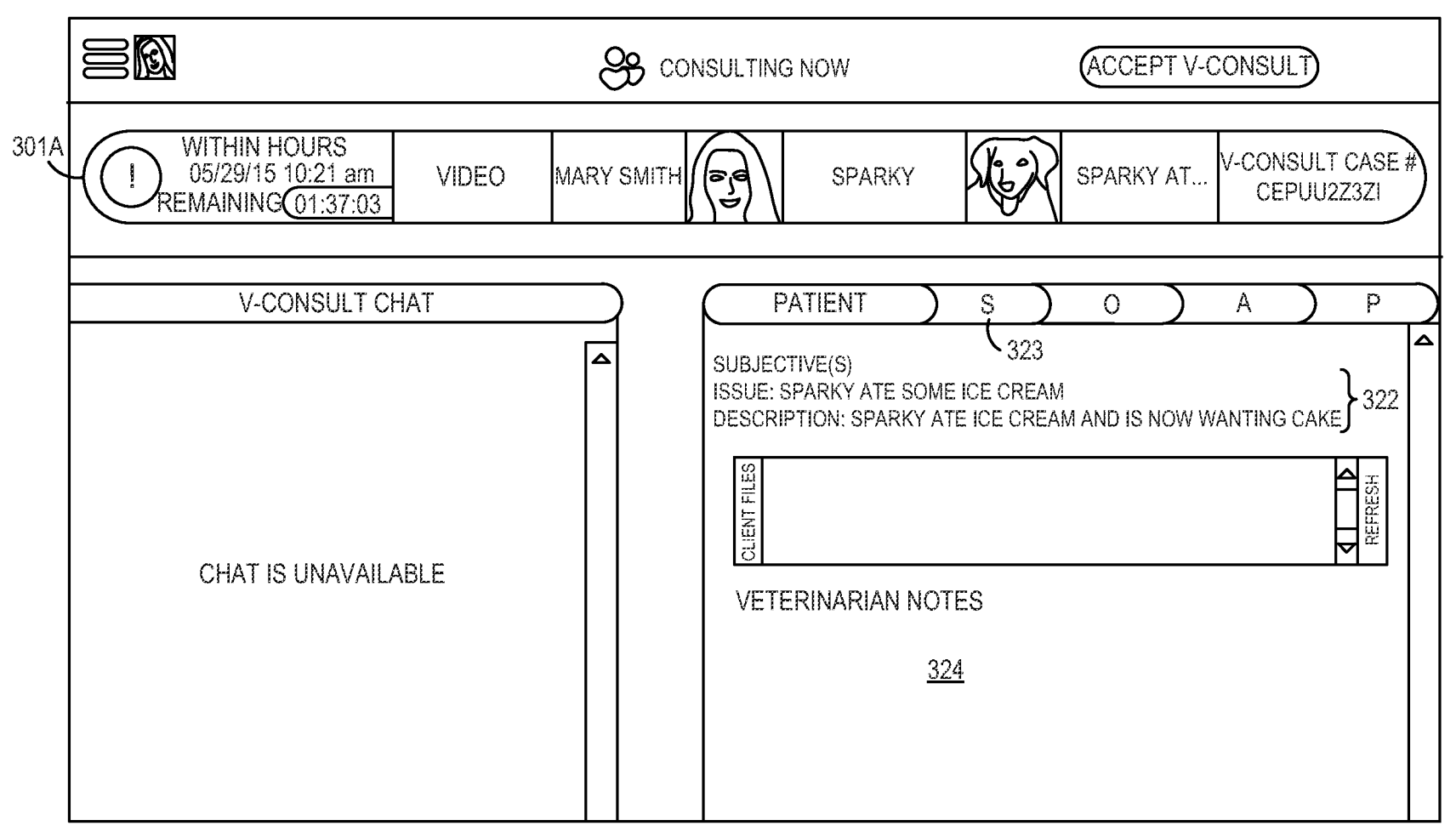

A veterinarian can select veterinary consult 301A to see more information. Turning, to FIG. 3B, FIG. 3B illustrates an example of how to enter subjective findings related to veterinary consults 301A. Issue and description 321 provide additional relevant information for veterinary consult 301A. Tab 323 "S" is selected providing a text field 324 for entering notes.

Figure 3C:
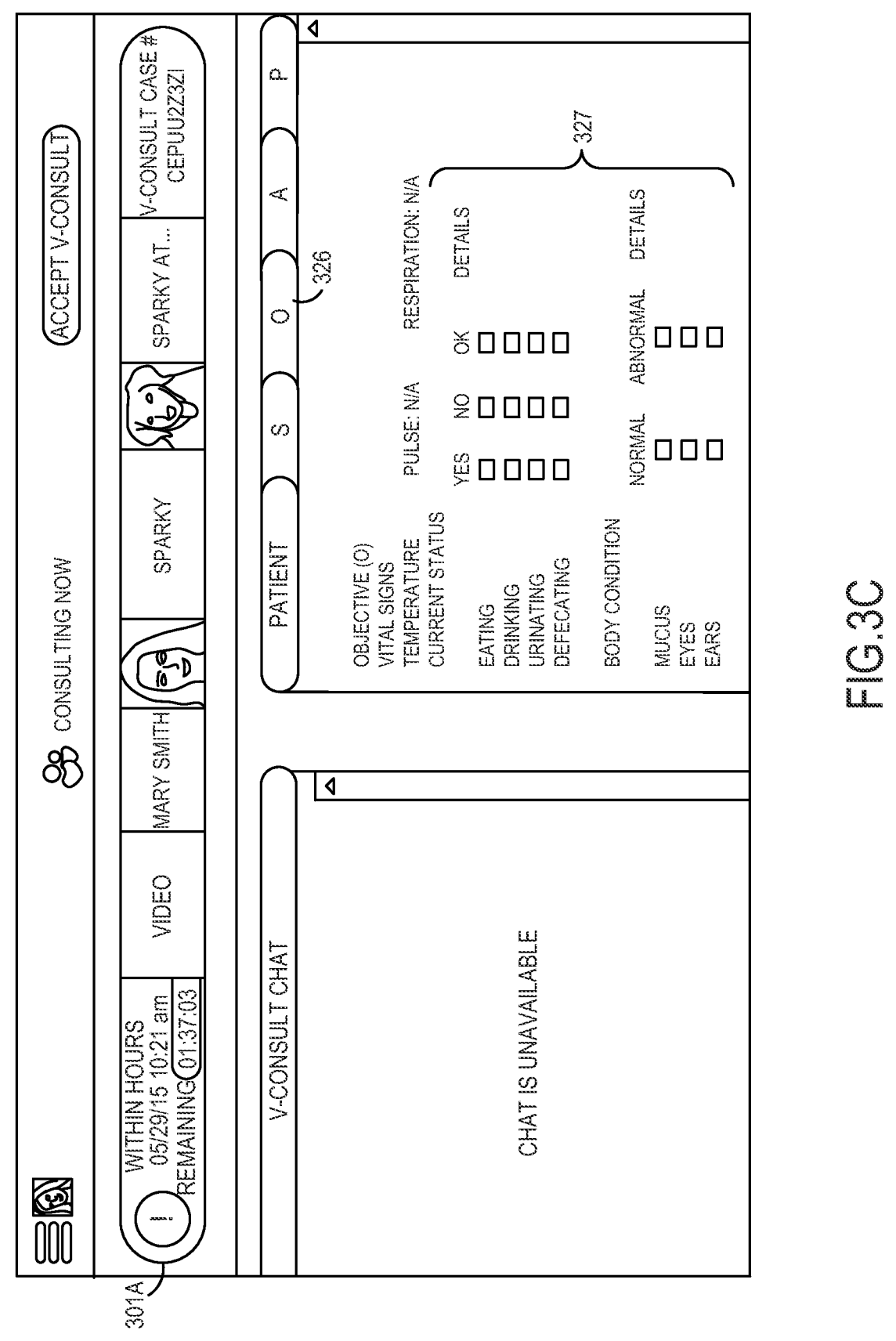

Turning to FIG. 3C, FIG. 3C illustrates an example of how to enter objective findings related a veterinary consult. Tab 326 "O" is selected providing check boxes 327 for indicating various objective findings.

Figure 3D:
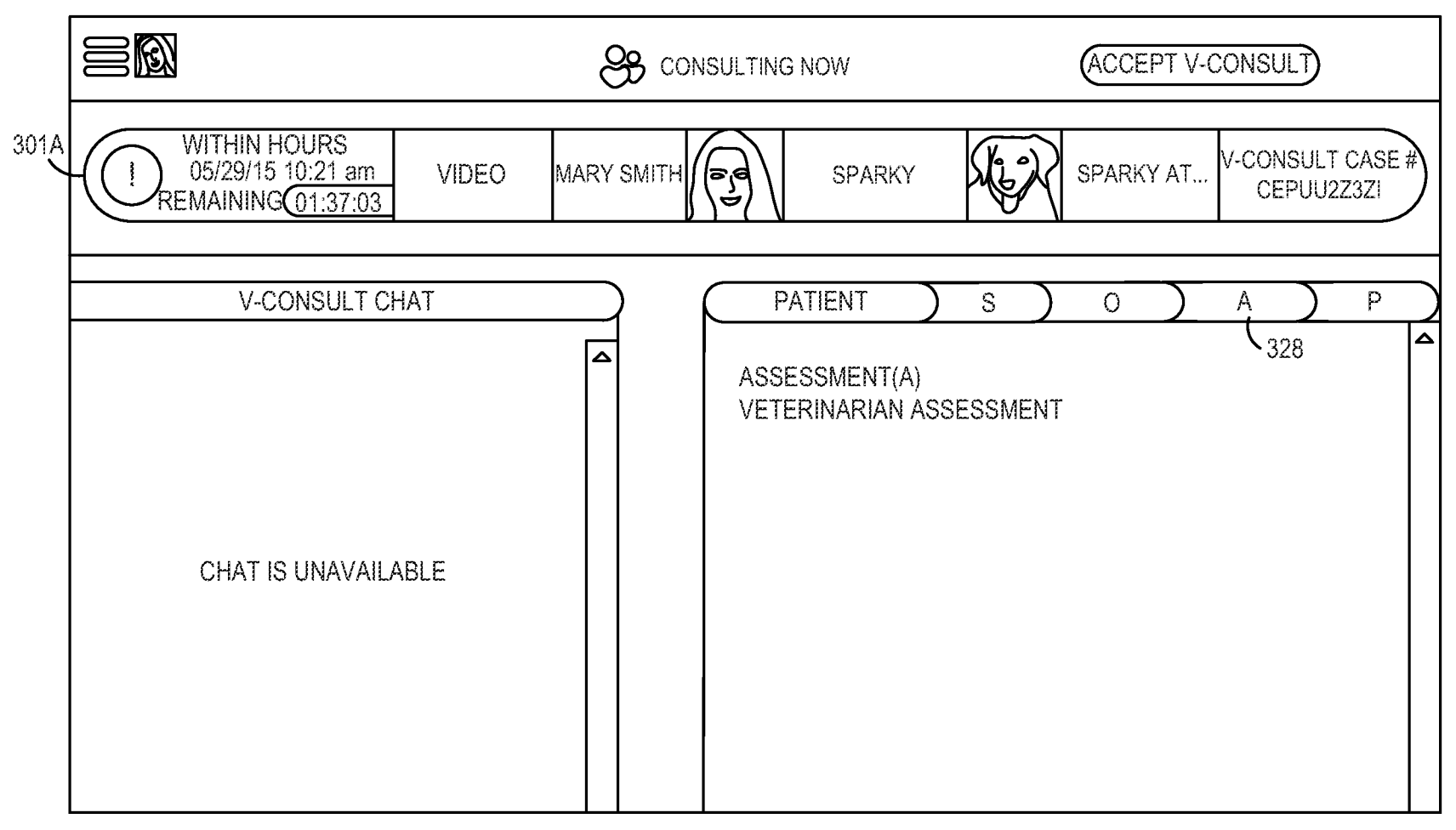

Turning to FIG. 3D, FIG. 3D illustrates an example of how to enter a veterinarian assessment related to veterinary consults 301A. Tab 328 "A" is selected providing an area to enter an assessment.

Figure 3E:
FIG. 3E illustrates an example of how to enter a plan related to a veterinary consult.

Turning to FIG. 3E, FIG. 3E illustrates an example of how to enter a plan related to veterinary consults 301A. Tab 329 "P" is selected providing an area 331 to enter notes and an area 332 to enter prescription information.

Figure 3F:
FIG. 3F illustrates an example of a selected veterinary consult.

After reviewing the veterinary consult 301, a veterinarian may choose to accept veterinary consult 301. FIG. 3F illustrates an example of a selected veterinary consult 301A. As depicted, the status of veterinary consult 301 is changed to accepted. Further, chat area 341 is activated to permit the client to chat with the veterinarian. Alternately, the veterinarian can activate video chat with the client by selecting button 342.

Figures 4D, 4E, 4F:
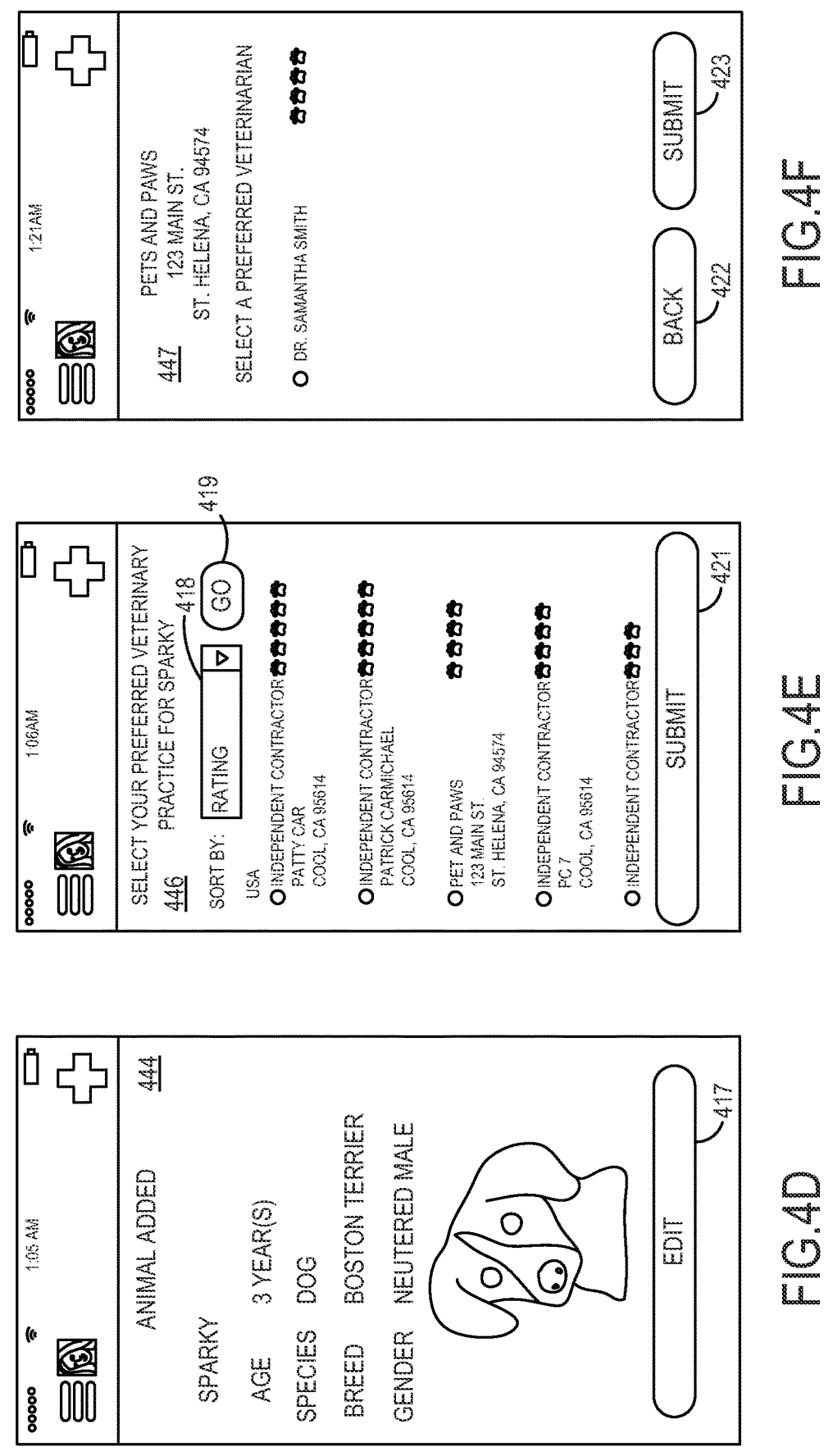
Figure 4G:
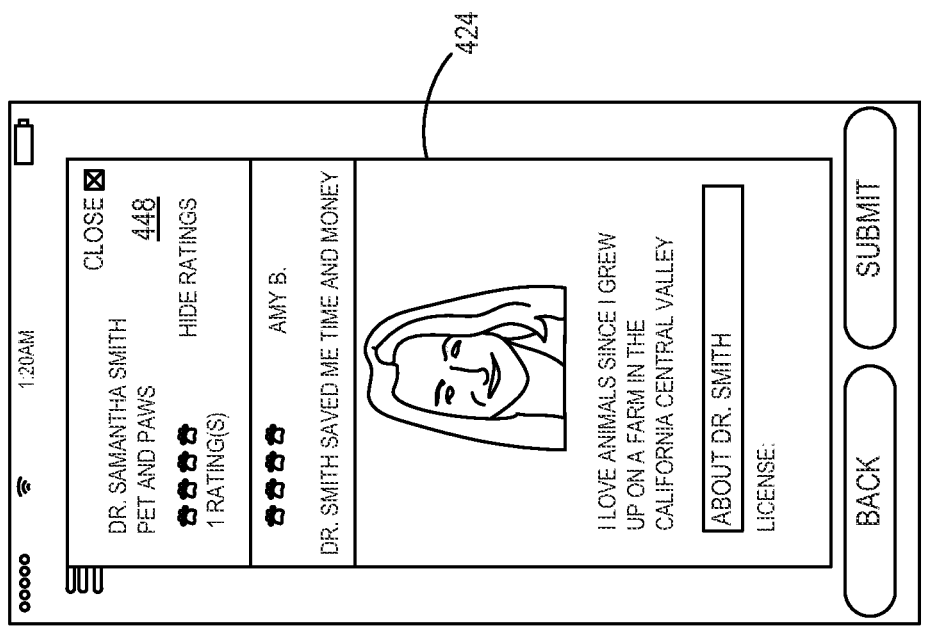

FIGS. 4A-4G illustrate user interface screens used to register a client with a network-based veterinary service provider. FIG. 4A illustrates a user interface screen 441 presenting text fields 410, 402, and 403 for entering email, username, and password respectively. When email, username, and password are entered, button 404 can be selected to continue with the registration process. Moving to FIG. 4B, illustrates a user interface screen 442 wherein various profile information can be entered by selected items from drop down lists 406 and 407

Moving to FIG. 4C, illustrates a user interface screen 442 wherein information about an animal can be added to a profile. An animals name can be entered into text field 408. The client can select age, species, breed, and gender of the animal using interface controls 409, 411, 412, and 423 respectively. Button 414 can be used to upload a picture of the animal. When complete, button 416 can be selected to add the animal to the client profile.

Moving to FIG. 4D, illustrates a user interface screen 444 wherein button 417 can be selected to edit information about the animal.

Moving to FIG. 4E, illustrates a user interface screen 446 wherein the client can select a preferred veterinary practice. The client can sort veterinary practices on various criteria (e.g., rating, geographical location, size, etc.) with user interface control 418 and button 419. When a veterinary practice is selected, button 421 can be selected to proceed. Moving to FIG. 4F, illustrates a user interface screen 447 wherein the client can select a particular veterinarian from those working at the selected veterinary practice. The client can select button 423 to submit selection of the veterinarian. If a desired veterinarian is not available, the client can select button 422 to return to screen depicted in FIG. 4E. Moving to FIG. 4G, FIG. 4G illustrates a user interface screen displaying information 424 about the selected veterinarian is displayed.

Figure 5E:
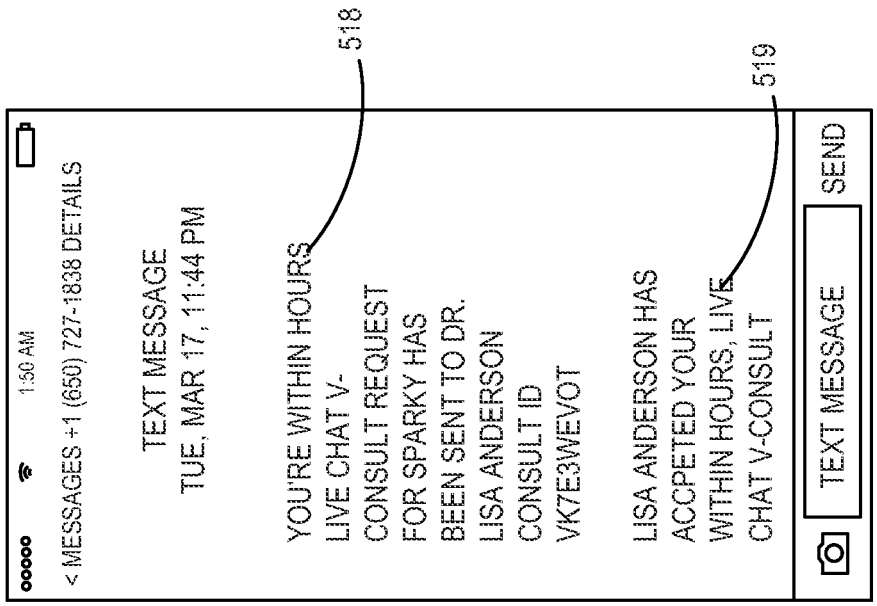

FIGS. 5A-5F illustrate user interface screens associated with requesting a veterinary consult. FIG. 5A illustrates a user interface screen 541 for initiating a veterinary consult request. User interface screen 541 depicts any pending, accepted, or completed veterinary consults for the client. Button 511 can be selected to indicate a desire for a new veterinary consult request. The client can select user interface control 502 to proceed. Moving to FIG. 5B, FIG. 5B illustrates user interface screen 542 for selecting the priority and communication method for the new veterinary consult request. The client can select user interface control 512 or 513 to choose between "urgent" and "within hours". The client can select user interface control 514 or 516 to choose between "video" or "chat". When selections are made, the client can select user interface control 504 to proceed. If the client decides not to create a new consult request, the client can select user interface control 503 to return to user interface screen 541.

Figure 5D:
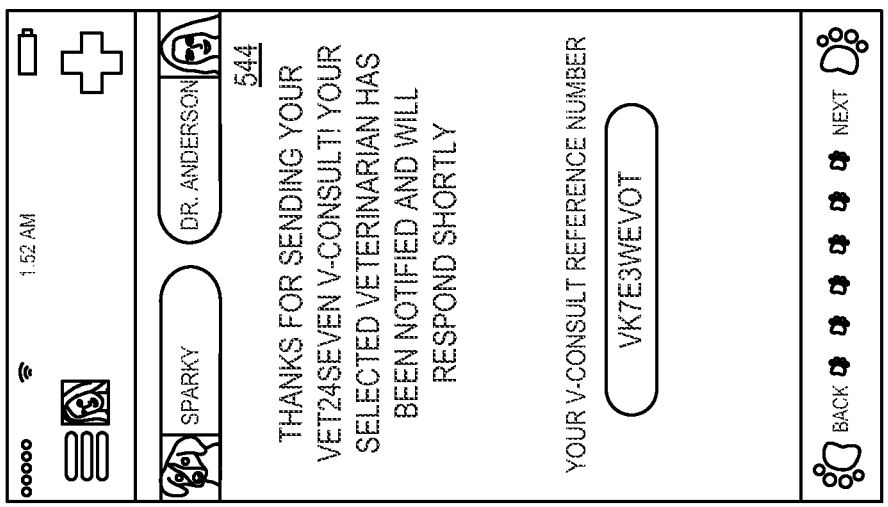

Moving to FIG. 5C, FIG. 5C illustrates user interface screen 543 presenting a consult price. The client can select check box 517 to agree to the consult price. When check box 517 is selected, the client can select user interface control 504 to proceed. If the client does not accept the price, the client can select user interface control 506 to return to user interface screen 542. User interface control 507 can be inactivated until check box 517 is selected. Moving to FIG. 5D, FIG. 5D illustrates a user interface screen 544 with confirmation information for the new consult request.

FIG. 5E illustrates text message updates for the new consult request. Message 518 indicates submission of the new consult request and message 519 indicates acceptance of the new consult request by the veterinarian. FIG. 5F illustrates an email with details of the new consult request.

FIGS. 6A-6F illustrate user interface screens used to register a veterinarian with a network-based veterinary service provider.

Figure 6A:
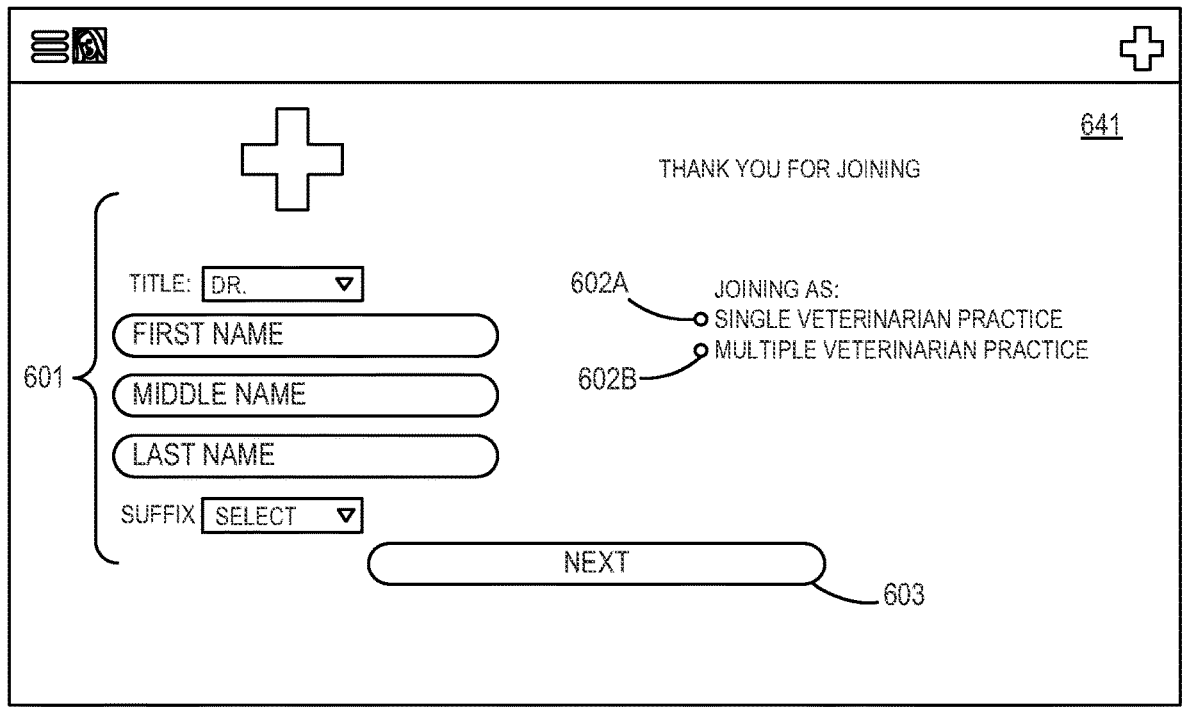
FIGS. 6A-6F illustrate user interface screens used to register a veterinarian with a network-based veterinary service provider.
Figure 6B:
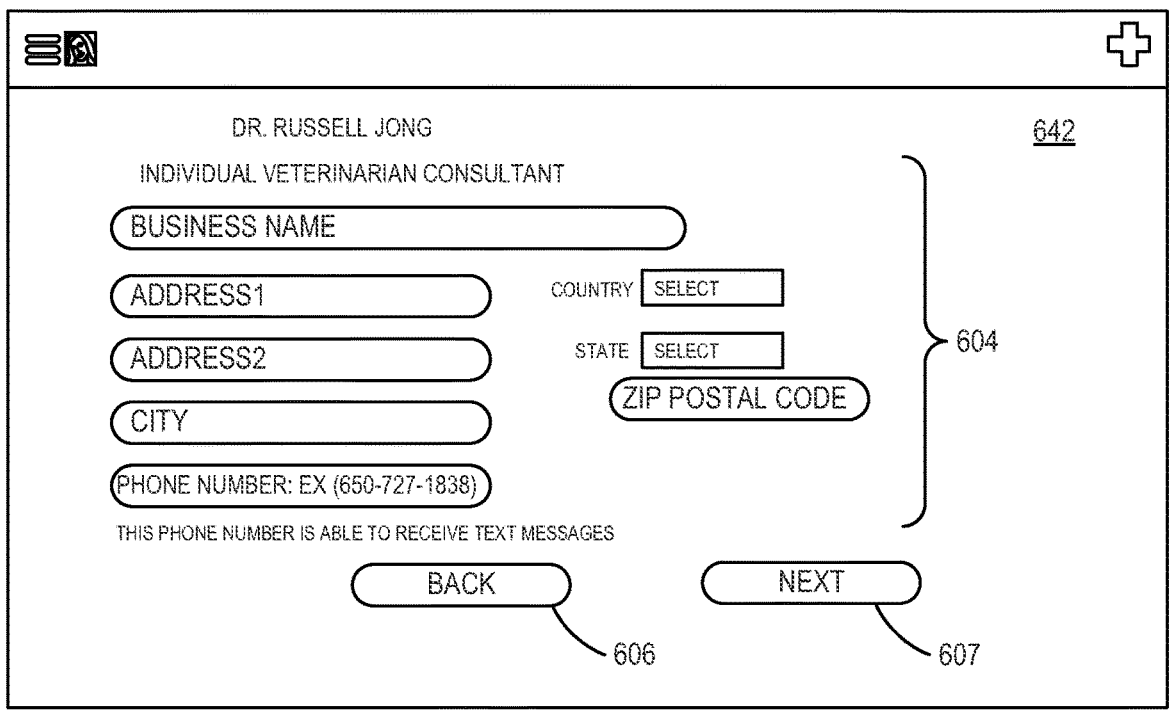

FIG. 6A illustrates a user interface screen 641 presenting user interface controls 601 wherein a veterinarian can enter name information. The veterinarian can then join as single veterinarian practice by selecting user interface control 602A or join as multiple veterinarian practice by selecting user interface control 602B. The veterinarian can select button 603 to go to the user interface screen 642. Moving to FIG. 6B, FIG. 6B illustrates user interface screen 642 presenting user interface controls 604 wherein the veterinarian can enter a business name and other business information for their practice. The veterinarian can select button 606 to go back to user interface screen 641 and can select button 607 to go to user interface screen 643.

Figure 6C:
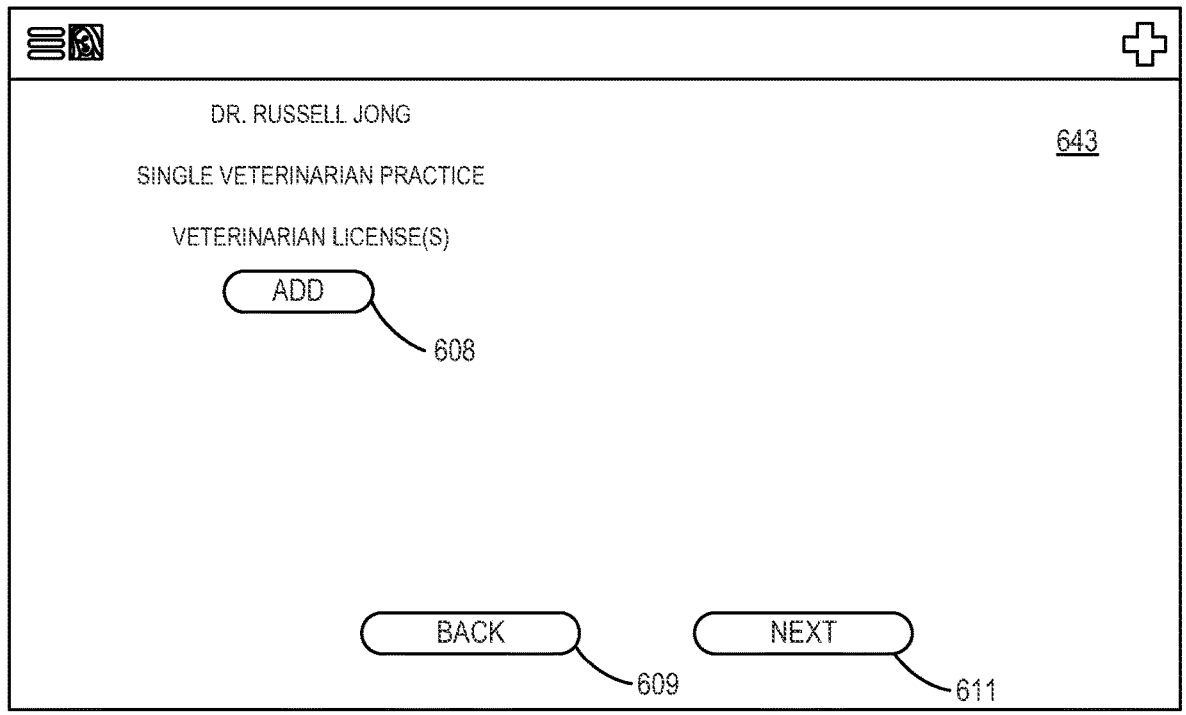
Figure 6D:
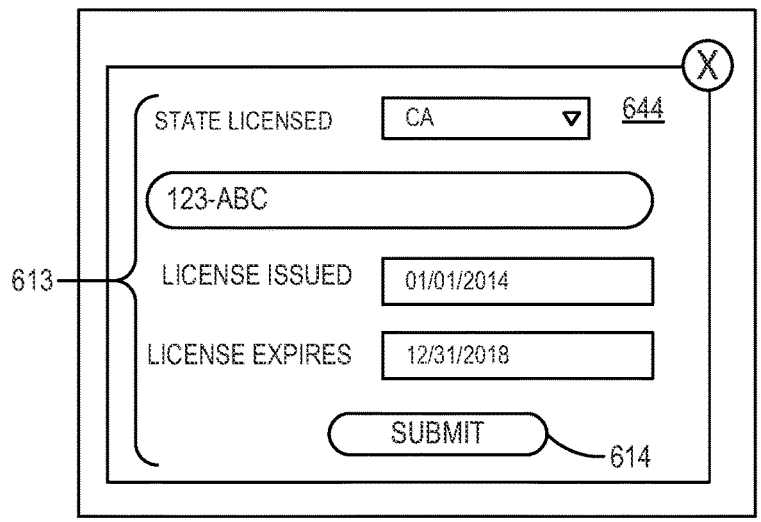

Moving to FIG. 6C, FIG. 6C illustrates user interface screen 643 wherein the veterinarian can add veterinary licenses. The veterinarian can select button 608 to add a veterinary license. Turning to FIG. 6D, selection of button 608 causes user interface 644 to be presented. The veterinarian can enter the relevant license information using user interface controls 613. When the information is entered, the veterinarian can select button 614 to submit the license. Selecting button 614 also returns control to user interface screen 643 where additional licenses can be added. The veterinarian can select button 609 to go back to user interface screen 642 and can select button 611 to go to user interface screen 646.

Figure 6E:
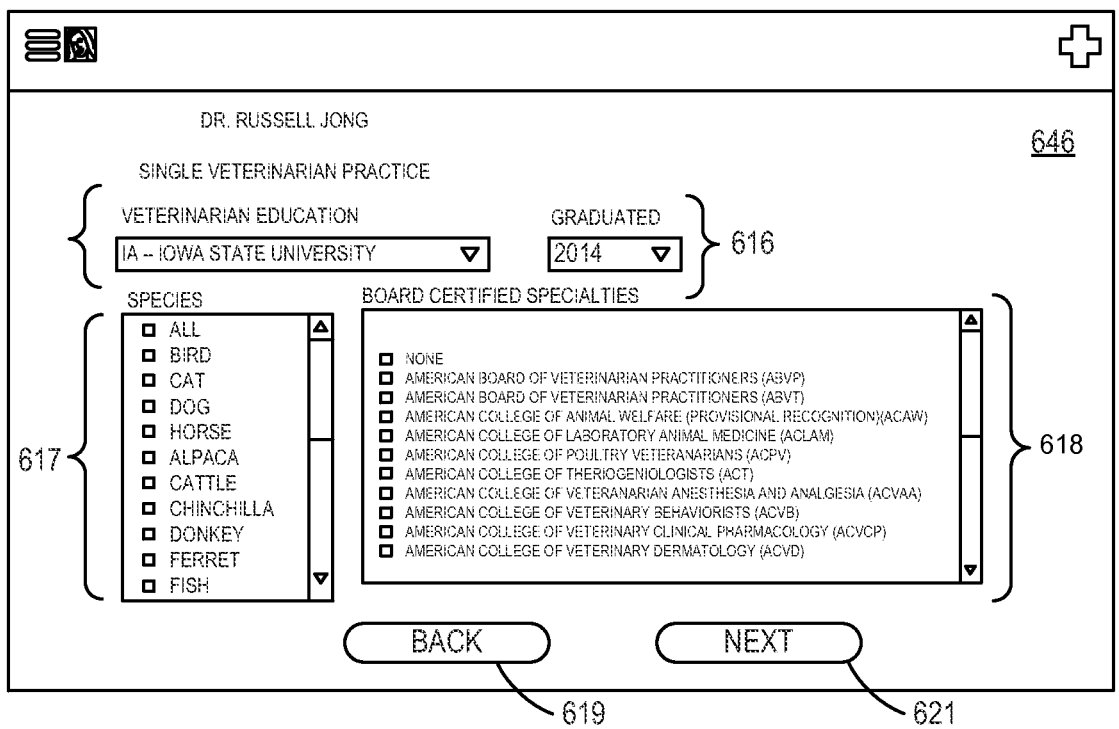

Moving to FIG. 6E, FIG. 6E illustrates user interface screen 646 wherein the veterinarian can enter academic credentials, species, and board certified specialties. The veterinarian can enter academic credentials using user interface controls 618. The veterinarian can select one or more species using user interface controls 617. The veterinarian can select one or more board certified specialties using user interface controls 618. The veterinarian can select button 609 to go back to user interface screen 643 and can select button 611 to go to user interface screen 647.

Figure 6F:
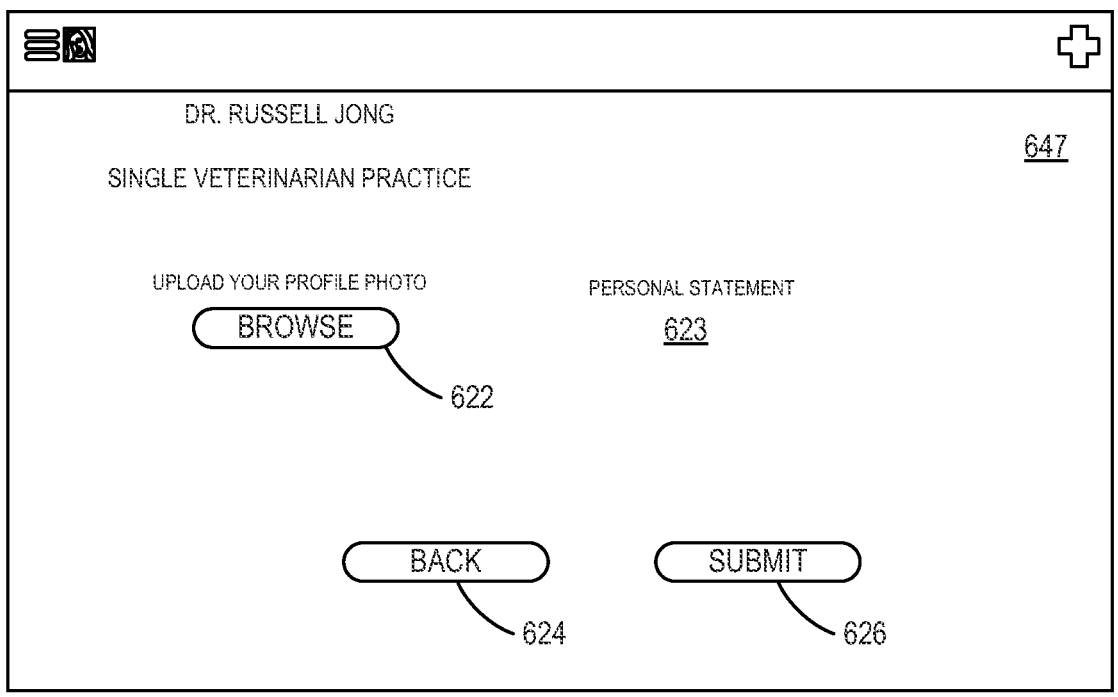

Moving to FIG. 6F, FIG. 6F illustrates user interface screen 647 for uploading a profile photo and typing a personal statement. The veterinarian can select button 622 to browse their device for a profile picture. The veterinarian can enter text of a personal statement into text field 623. The veterinarian can select button 624 to go back to user interface screen 646 and can select button 611 to go submit their profile to the network-based veterinary service provider.

FIG. 7A illustrates availability for a veterinarian. A consult module, such as, for example, consult module 103 can consider availability when identifying relevant veterinarians capable of handling a veterinary consult request.

FIG. 7B illustrates a pricing matrix for a veterinarian. When a consult module identifies a veterinarian for handling a veterinary consult request, the consult module can present the rate to the client for approval.

In aspects, a client may have a preferred veterinarian. A consult module (e.g., 103) can direct the clients' veterinary consults to the preferred veterinarian when available. When a preferred veterinarian is not available, the consult module can provide the client with alternate veterinarians capable of handling a particular veterinary consult. In a multiple veterinarian practice, alternate veterinarian can be another veterinarian in the same practice. When no other veterinaries are available from the same practice (e.g., when a clinic is closed), the consult module can identify other alternate veterinarians. An alternate veterinarian can be selected based on one or more of: geographic location, licensure, availability, ratings, number of consults performed, species treated, as well as any other information contained in a veterinarian or practice profile.

Although the components and modules illustrated herein are shown and described in a particular arrangement, the arrangement of components and modules may be altered to process data in a different manner. In other embodiments, one or more additional components or modules may be added to the described systems, and one or more components or modules may be removed from the described systems. Alternate embodiments may combine two or more of the described components or modules into a single component or module.

The foregoing description has been presented for the purposes of illustration and description. It is not intended to be exhaustive or to limit the invention to the precise form disclosed. Many modifications and variations are possible in light of the above teaching. Further, it should be noted that any or all of the aforementioned alternate embodiments may be used in any combination desired to form additional hybrid embodiments of the invention.

Further, although specific embodiments of the invention have been described and illustrated, the invention is not to be limited to the specific forms or arrangements of parts so described and illustrated. The scope of the invention is to be defined by the claims appended hereto, any future claims submitted here and in different applications, and their equivalents.

What is claimed:

1. A method for providing remote veterinary medical analysis, comprising:
    receiving, via network communication, a veterinary consult request including veterinary consult request data from a client mobile device, the veterinary consult request data comprising multimedia content including at least one of a picture or a video of a condition of an animal captured at the client mobile device, the veterinary consult request data indicated by a previously registered client that previously registered with a veterinary consult system and including: an animal species of the animal, a veterinary consult urgency, and a desired digital communication method;
    accessing, from a database, veterinarian data for plurality of previously registered veterinarians that previously registered with the veterinarian consult system, the veterinarian data including, for each previously registered veterinarian included in the plurality of previously registered veterinarians: an address, availability, animal species treated, credentials, licenses, specialties, and a pricing matrix;
    matching a registered veterinarian, from among the plurality of previously registered veterinarians, to the veterinary consult request based on the veterinary consult request data and veterinarian data of the registered veterinarian;
    enabling the registered veterinarian to scroll through the multimedia content, including the at least one of the picture or the video of the condition of the animal, on an online dashboard and select the veterinary consult request;
    accessing a pricing matrix corresponding specifically to the registered veterinarian and relating different combinations of a plurality of veterinary consult urgency levels and a plurality of digital communication methods to a plurality of veterinary consult fee options;
    determining a veterinary consult fee for the registered veterinarian to respond to the veterinary consult request in accordance with the pricing matrix and based on the veterinary consult urgency and the desired digital communication method;
    notifying the client of the veterinary consult fee;
    preauthorizing a charge to a credit card of the previously registered client for the previously registered veterinarian to respond to the veterinary consult request contingent upon previously registered client's acceptance of the veterinary consult fee;
    receiving the previously registered client's acceptance of the veterinary consult fee subsequent to the preauthorization; and
    a processor automatically:
        allocating communication resources enabling the client mobile device to exchange further communication regarding the condition of the animal with the registered veterinarian at an agreed to time using the desired digital communication method contingent upon the previously registered client's acceptance; and
        communicating animal diagnostic information related to the condition of the animal from the registered veterinarian to the client mobile device via the desired digital communication method subsequent to the previously registered client's acceptance.

2. The method of claim 1, wherein accessing a pricing matrix corresponding specifically to the registered veterinarian comprises accessing the pricing matrix from the veterinarian data of the registered veterinarian.

3. The method of claim 1, wherein the veterinary consult request further includes a description of the condition of the animal.

4. The method of claim 1, further comprising;
    accessing client data for the previously registered client from the database; and
    including the client data in the veterinary consult request.

5. The method of claim 4, wherein accessing client data comprises accessing a preferred veterinarian for the previously registered client.

6. The method of claim 5 wherein matching a previously registered veterinarian to the veterinary consult request comprises matching the preferred veterinarian to the veterinary consult request.

7. The method of claim 4, wherein accessing client data comprises accessing client data that was entered by the previously registered client during a registration process.

8. The method of claim 1, wherein accessing the veterinarian data comprises accessing the veterinarian data that was entered by the registered veterinarian during a registration process.

9. The method of claim 1, wherein communicating animal diagnostic information comprises exchanging text messages in a chat session and participating in a video chat session.

10. A computer program product for providing remote veterinary medical analysis, the computer program product comprising a non-transitory computer-readable storage medium having computer-usable program code embodied therein, the computer-usable program code configured to perform the following when executed by at least one processor:
receive, via network communication, a veterinary consult request including veterinary consult request data from a client mobile device, the veterinary consult request data comprising multimedia content including at least one of a picture or a video of a condition of an animal captured at the client mobile device, the veterinary consult request data indicated by a previously registered client that previously registered with a veterinary consult system and including a client indicated: an animal species of the animal, a veterinary consult urgency and a desired digital communication method;
access, from a database, veterinarian data for a plurality of previously registered veterinarians that previously registered with the veterinarian consult system, the veterinarian data including, for each previously registered veterinarian included in the plurality of previously registered veterinarians: an address, availability, animal species treated, credentials, licenses, specialties, and a pricing matrix;
match a registered veterinarian, from among the plurality of previously registered veterinarians, to the veterinary consult request based on the veterinary consult request data and veterinarian data of the registered veterinarian;
enable the registered veterinarian to scroll through the multimedia content, including the at least one of the picture or the video of the condition of the animal, on an online dashboard and select the veterinary consult request;
access a pricing matrix corresponding specifically to the registered veterinarian and relating different combinations of a plurality of veterinary consult urgency levels and a plurality of digital communication methods to a plurality of veterinary consult fee options;
determine a veterinary consult fee for the registered veterinarian to respond to the veterinary consult request in accordance with the pricing matrix and based on the veterinary consult urgency and the desired digital communication method;
notify the client of the veterinary consult fee;
preauthorize a charge to a credit card of the previously registered client for the previously registered veterinarian to respond to the veterinary consult request contingent upon previously registered client's acceptance of the veterinary consult fee;
receive the previously registered client's acceptance of the veterinary consult fee subsequent to the preauthorization; and
automatically:
allocate communication resources enabling the client mobile device to exchange further communication regarding the condition of the animal with the registered veterinarian at an agreed to time using the desired communication method contingent upon the previously registered client's acceptance; and
communicating animal diagnostic information related to the condition of the animal from the registered veterinarian to the client mobile device via the desired digital communication method subsequent to the previously registered client's acceptance.

11. The computer program product of claim 10, wherein the computer-usable program code is further configured to:
receive an indication via network communication that the registered veterinarian accepted the veterinary consult request; and
notify the client via network communication that the veterinary consult request was accepted.

12. The computer program product of claim 10, wherein the computer-usable program code is further configured to:
access client data for the previously registered client from database; and
include the client data in the veterinary consult request.

13. The computer program product of claim 12, wherein computer-usable code configured to access client data comprises computer-usable code configured to accessing a preferred veterinarian for the previously registered client.

14. The computer program product of claim 13, wherein computer-usable code configured to match a previously registered veterinarian to the veterinary consult request comprises computer-usable code configured to match the preferred veterinarian to the veterinary consult request.

15. A veterinary medical analysis system, comprising:
at least one processor;
at least one memory device operably coupled to the at least one processor and storing instructions for execution on the at least one processor, the instructions causing the at least one processor to:
receive, via network communication, a request for a veterinary consult request including veterinary consult request data from a client mobile device, the veterinary consult request data comprising multimedia content including at least one of a picture or a video of a condition of an animal captured at the client mobile device, the veterinary consult request data indicated by a previously registered client that previously registered with a veterinary consult system and including: an animal species of the animal, a veterinary consult urgency, and a desired digital communication method;
access, from a database, veterinarian data for a plurality of previously registered veterinarians that previously registered with the veterinarian consult system, the veterinarian data including, for each previously registered veterinarian included in the plurality of previously registered veterinarians: an address, availability, animal species treated, credentials, licenses, specialties, and a pricing matrix;
match a registered veterinarian, from among the plurality of previously registered veterinarians, to the veterinary consult request based on the veterinary consult request data and veterinarian data of the registered veterinarian;

enable the registered veterinarian to scroll through the multimedia content, including the at least one of the picture or the video of the condition of the animal, on an online dashboard and select the veterinary consult request;

access a pricing matrix corresponding specifically to the registered veterinarian and relating different combinations of a plurality of veterinary consult urgency levels and a plurality of digital communication methods to a plurality of veterinary consult fee options;

determine a veterinary consult fee for the previously registered veterinarian to respond to the veterinary consult request in accordance with the pricing matrix and based on the veterinary consult urgency and the desired digital communication method;

notify the client of the veterinary consult fee;

preauthorize a charge to a credit card of the previously registered client for the previously registered veterinarian to respond to the veterinary consult request contingent upon previously registered client's acceptance of the veterinary consult fee;

receive the previously registered client's acceptance of the veterinary consult fee; and automatically:

allocate communication resources enabling the client mobile device to exchange further communication regarding the condition of the animal with the registered veterinarian at an agreed to time using the desired digital communication method contingent upon the previously registered client's acceptance; and communicate animal diagnostic information related to the condition of the animal from the registered veterinarian to the client mobile device via the desired digital communication method subsequent to the previously registered client's acceptance.

16. The veterinary medical analysis system of claim 15, wherein the instructions further cause the at least one processor to:

receive an indication via network communication that the registered veterinarian accepted the veterinary consult request; and notify the client via network communication that the veterinary consult request was accepted.

17. The veterinary medical analysis system of claim 15, wherein instructions configured to communicate animal diagnostic information comprise instructions configured to the communication methods include exchanging text messages in a chat session and participate in a video chat session.

* * * * *

UNITED STATES PATENT AND TRADEMARK OFFICE
CERTIFICATE OF CORRECTION

PATENT NO. : 10,741,292 B2  
APPLICATION NO. : 14/740044  
DATED : August 11, 2020  
INVENTOR(S) : Lai et al.

Page 1 of 1

It is certified that error appears in the above-identified patent and that said Letters Patent is hereby corrected as shown below:

In the Claims

Column 13, Claim 10, Line 34 the phrase "a client indicated" should be removed.

Column 16, Claim 17, Line 21 the phrase "configured to the communication methods include" should be removed.

Signed and Sealed this  
Tenth Day of August, 2021

Drew Hirshfeld  
*Performing the Functions and Duties of the*  
*Under Secretary of Commerce for Intellectual Property and*  
*Director of the United States Patent and Trademark Office*